(12) United States Patent
Ripplinger et al.

(10) Patent No.: US 8,669,384 B2
(45) Date of Patent: Mar. 11, 2014

(54) PROCESS FOR PREPARING DIVINYLARENE DIOXIDES

(75) Inventors: Eric B. Ripplinger, Lake Jackson, TX (US); David Jean, Friendswood, TX (US); David Burow, Taylor, TX (US); Khiet Pham, Lake Jackson, TX (US); Maurice Marks, Lake Jackson, TX (US); Gyongyi Gulyas, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 13/581,333

(22) PCT Filed: Mar. 4, 2011

(86) PCT No.: PCT/US2011/027102
§ 371 (c)(1),
(2), (4) Date: Nov. 13, 2012

(87) PCT Pub. No.: WO2011/112426
PCT Pub. Date: Sep. 15, 2011

(65) Prior Publication Data
US 2013/0123521 A1 May 16, 2013

(51) Int. Cl.
*C07D 301/06* (2006.01)

(52) U.S. Cl.
USPC ........................................ 549/524

(58) Field of Classification Search
USPC ........................................ 549/524
See application file for complete search history.

(56) References Cited

U.S. PATENT DOCUMENTS

| | | |
|---|---|---|
| 2,977,374 A | 3/1961 | Phillips et al. |
| 6,048,513 A | 4/2000 | Quarderer et al. |

FOREIGN PATENT DOCUMENTS

JP 9286150 A 11/1997

OTHER PUBLICATIONS

Ran C et al. "Synthesis of C2 benzo pyrene and its 7,8-dihydrodiol and 7,8-dione implicated as carcinogenic metabolites" Tetrahedron Letters, Elsevier, Amsterdam, NL. vol. 49, No. 29-30, Jul. 21, 2008, pp. 4531-4533, XP0227131,96. J. Tetiet.
Hoppf et al.,Helvetica Chim. Acta (1957) 40,274.
Gancarlo Berti "Stereochem I CAL Aspects of the synthesis of 1.2 epoxides" Topics in Stereochemistry, Wiley, New York, NY US, vol. 7, Jan. 1, 1973, pp. 93-251.
M. Worzakowska, J. Appl Poly Sci (2007) vol. 103, 462-469.

*Primary Examiner* — Taylor Victor Oh

(57) ABSTRACT

A process for preparing a divinylarene dioxide including (a) reacting at least one divinylarene with hypochlorous acid to form a chlorohydrin; and (b) treating the chlorohydrin formed in step (a) with at least one base, under conditions to form a divinylarene dioxide product.

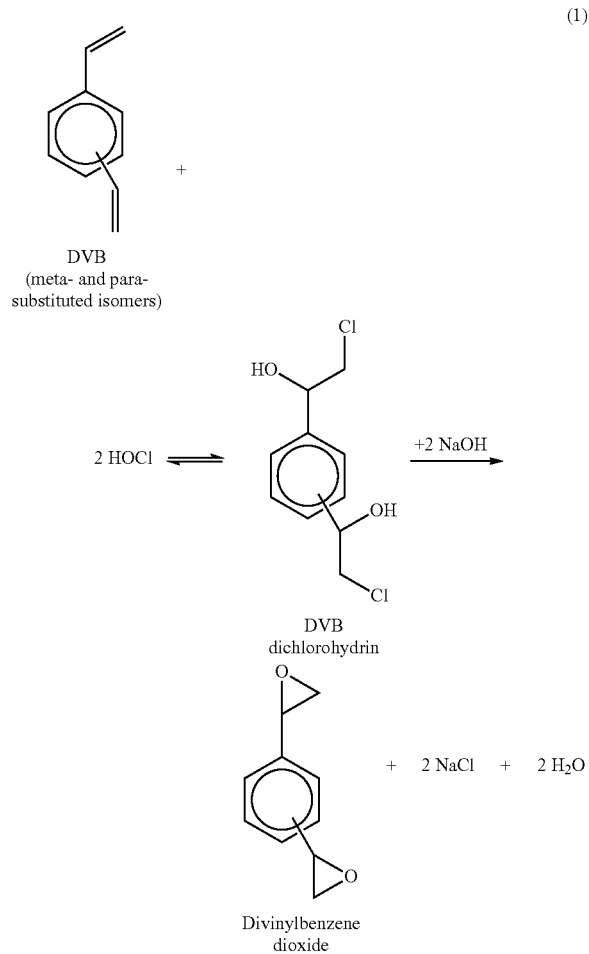

14 Claims, No Drawings

PROCESS FOR PREPARING DIVINYLARENE DIOXIDES

BACKGROUND OF THE INVENTION

1. Field of the Invention

The present invention is related to a process for preparing divinylarene dioxides, such as for example divinylarene dioxides derived from divinylbenzene. More specifically, the present invention relates to a process for preparing a divinylarene dioxide by utilizing a chlorohydrin route.

2. Description of Background and Related Art

Divinylarene dioxides, particularly divinylbenzene dioxide (DVBDO) and others which are derived from divinylbenzene (DVB) are a class of diepoxides which can be used as either reactive diluents or the main epoxy resin matrix in epoxy thermoset formulations. DVBDO itself has a very low liquid viscosity (for example less than about 20 centipoise [0.02 Pa-s]) making DVBDO especially useful in the preparation of low viscosity epoxy formulations. The epoxy formulations made from DVBDO are useful as intermediates in the production of various other products. For example, epoxy formulations made from DVBDO are suitable for use in the fields of coatings, composites, and molding compositions.

In general, the production of divinylarene dioxide can be accomplished by a variety of different methods. For instance, some of the prior art methods include: (1) oxidation by peroxy carboxylic acids; or (2) oxidation by hydrogen peroxide with a catalyst. For example, M. Worzakowska, J. Appl Poly Sci (2007) vol. 103, 462-469, discloses epoxidizing DVB by a method using acetonitrile-hydrogen peroxide with magnesium oxide catalyst and greater than a 4 fold molar excess of hydrogen peroxide to olefin. U.S. Pat. No. 2,977,374 also discloses epoxidizing DVB using peracetic acid in ethyl acetate and reports a DVBDO yield of 49%.

Hoppf et al., Helvetica Chim Acta (1957) 40, 274 teaches the use of chlorohydrins and base to produce DVBDO; however, the chlorohydrins are generated by the reduction of chloroacetylbenzenes with lithium aluminium hydride.

None of the heretofore known processes disclose the successful preparation of divinylarene dioxides using hypochlorous acid to produce the chlorohydrin, followed by base treatment to produce the epoxide at high yields.

SUMMARY OF THE INVENTION

The present invention involves simple chemicals such as a hypochlorous acid and a base to prepare a divinylarene dioxide. The present invention advantageously provides a process for successfully preparing divinylarene dioxides at high yields (e.g. greater than about 40%).

One embodiment of the present invention is directed to a two-step reaction process for preparing a divinylarene dioxide including (1) a chlorohydrin formation reaction step using hypochlorous acid; and (2) a dehydrohalogenation step using an alkali metal hydroxide to convert the chlorohydrin to an epoxide. The process of the present invention may be illustrated by the following chemical reaction scheme:

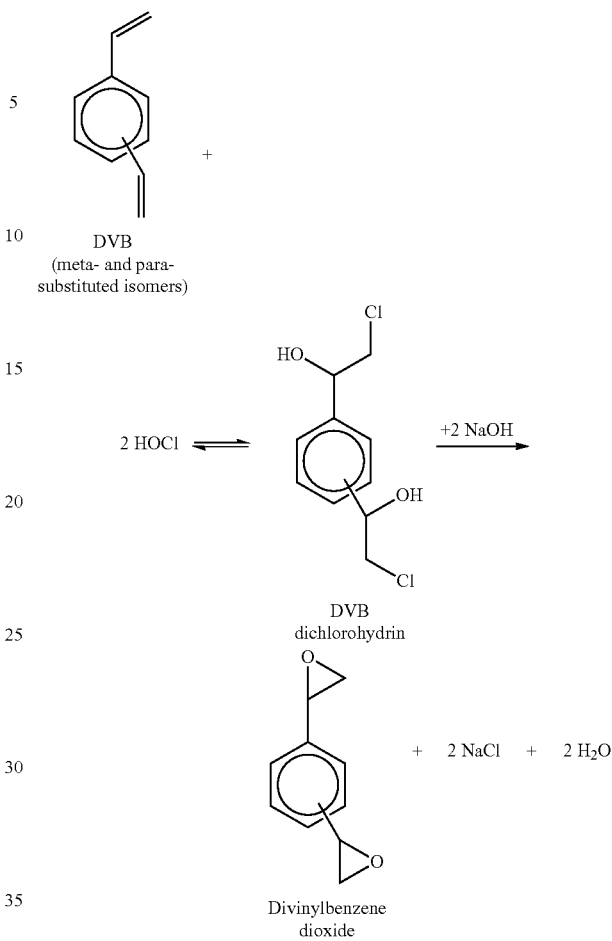

In one embodiment the process for preparing a divinylarene dioxide includes the two-step process of (a) reacting at least one divinylarene with hypochlorous acid to form a chlorohydrin, in the presence of a water-miscible hypochlorination solvent; wherein the resulting reaction mixture comprises a homogeneous solution; and (b) dehydrochlorination of the chlorohydrin of step (a) to an epoxide such as a divinylarene dioxide product. In the present invention, the term homogeneous solution for the chlorohydrin formation step is defined as a solution that is clear to the eye with only one liquid phase, and with no solid present.

In another embodiment, the dehydrohalogenation step of the above synthesis of divinylarene dioxides is the conversion of chlorohydrins to epoxides by for example, treating the chlorohydrin formed in the first step (a) with at least one base and optionally, in the presence of at least one dehydrohalogenation solvent and optionally, in the presence of at least one phase transfer agent, under conditions to form a divinylarene dioxide product.

The process of the present invention provides a simple and an economical way to produce divinylarene dioxides. For example, in one embodiment, the present invention process is particularly suited for the preparation of DVBDO, a very low viscosity liquid epoxy resin, from DVB.

Advantageously, the present invention process is carried out under conditions such that the co-production of undesirable by-products is minimized In addition, the process of the present invention advantageously produces divinylarene dioxides in high yields, for example, in yields of greater than about 40% and preferably greater than about 50% based on starting divinylarene.

DETAILED DESCRIPTION OF THE INVENTION

In its broadest scope, the present invention comprises a process for preparing a divinylarene dioxide including the steps of:

(a) reacting at least one divinylarene with hypochlorous acid to form a chlorohydrin, in the presence of water and optionally in the presence of a solvent; wherein the resulting reaction mixture comprises a homogeneous solution; and (b) treating the chlorohydrin formed in step (a) with at least one base, under conditions to form a divinylarene dioxide product.

The reaction steps may include other optional components such as at least one solvent; or other desirable additives which do not detrimentally affect the formation of a divinylarene dioxide. The reaction may be batch or continuous; and the reactants are allowed to react under conditions to produce the corresponding divinylarene dioxide. Once the product is formed, the resulting divinylarene dioxide product may optionally be purified, for example, by distillation, crystallization, and other known purification methods known in the art.

As an illustration of one embodiment of the present invention, for example, a divinylarene dioxide such as divinylbenzene dioxide is prepared by reacting a divinylbenzene with hypochlorous acid, in the presence of a solvent such as acetone; wherein the resulting reaction mixture comprises a homogeneous solution to form a chlorohydrin. Then the chlorohydrin is subsequently treated with sodium hydroxide to obtain the epoxide (the divinylarene dioxide). The resulting aqueous layer with a salt by-product may be removed from the product to provide the usable epoxide product. If desired, optionally the epoxide product may subsequently be purified by known means such as distillation, crystallization, and the like.

The chlorohydrins of the present invention are produced by a chlorohydrin formation reaction step also referred to herein as a hypochlorination reaction step including contacting a divinylarene with hypochlorous acid, in the presence of water and optionally in the presence of a solvent; and further optionally, in the presence of a surfactant. In one embodiment, the resulting reaction mixture may comprise a homogeneous solution. By homogeneous solution it is meant a solution that is clear to the eye with only one liquid phase, and with no solid visibly present.

The source of divinylarene useful in the present invention may come from any known sources and particular to known processes for the preparation of divinylarenes. For example, divinylarenes can be prepared with salt or metal wastes from arenes and ethylene.

In one embodiment of the present invention, the divinylarene useful in the present invention may comprise any substituted or unsubstituted arene nucleus bearing two vinyl groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of oxidation-resistant groups including for example saturated alkyl, aryl, halogen, nitro, isocyanate, or RO— (where R may be saturated alkyl or aryl), or mixtures thereof. Ring-annulated benzenes may include for example naphthalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by the dehydrogenation of diethylbenzene (DEB) may contain quantities of ethylvinylbenzene (EVB) and DEB.

The divinylarene used in the process of the present invention may include for example divinylbenzene, divinylnaphthalene, divinylbiphenyl, divinyldiphenylether; and mixtures thereof.

The concentration of the divinylarene used in the present invention may range generally from about 0.5 weight percent (wt %) to about 90 wt %, preferably from about 1 wt % to about 10 wt %, and more preferably from about 1 wt % to about 5 wt % based on the total weight of the composition.

The hypochlorous acid (HOCl) used in the present invention may include any known available HOCl product; or alternatively, the HOCl used in the present invention may be made by any commonly known processes such as for example the process disclosed in U.S. Pat. No. 6,048,513; incorporated herein by reference.

In another embodiment, the HOCl may be produced in situ in the process of the present invention such as for example by adding water and chlorine to the reaction mixture by standard methods well known in the art. The in situ process for producing the HOCl may include the reaction of an alkali metal hypochlorite and an acid.

The process wherein the alkali metal hypochorite comprising sodium hypochorite, calcium hypochlorite, or mixtures thereof; and the acid is alkali metal bicarbonate, carbon dioxide, or mixtures thereof; and wherein the alkali metal bicarbonate is sodium bicarbonate.

In one embodiment, an aqueous HOCl may be used such as a dilute solution with water, for example in a concentration of from about 3 wt % to about 10 wt %.

The HOCl may optionally be adjusted to a pH level of about 3 to about 7 with a pH control agent or compound such as a base compound including for example sodium hydroxide. Most preferably, the pH of the HOCl solution is from about 3 to about 6.

The mole ratio of HOCl to olefinic C=C groups of the divinylarene used in the present invention may range from about 0.5 to about 1.5, more preferably from about 0.75 to 1.25 and most preferably from about 0.9 to about 1.1.

The water used in the preparation of the hypochlorous acid solution, or in the dilution of the reaction mixture, may be any water but preferably deionized water is used.

The total water used in the chlorohydrin formation reaction of the present invention, including water added with the HOCl solution and any additional water added, can range from about 5 parts by weight to about 50 parts by weight, and more preferably from about 20 parts by weight to about 30 parts by weight per every 1 part by weight of divinylarene used.

The process wherein the hypochlorous acid consists of a solution of hypochlorous acid dissolved in an organic solvent; wherein said hypochlorous acid solution is essentially free of chloride ions; and wherein said hypochlorous acid solution is obtained by extracting hypochlorous acid from a hypochlorous acid reaction mixture with the organic solvent; and wherein the solution of hypochlorous acid in organic solvent contains from about 0.1 to about 50 percent by weight of hypochlorous acid.

The reaction of step (a) above may include a hypochlorination solvent. The optional hypochlorination solvent useful in the present invention may include for example at least a partially water-miscible solvent and preferably a substantially water miscible solvent. In addition, preferably the solvent may be inert or non-reactive to the other reactants in the reaction mixture. For example, the solvent may include ketones such as methylethyl ketone and acetone; and mixtures of two or more ketones. Most preferably, acetone is used as the solvent in the present invention.

In general, the concentration of the solvent is sufficient to provide a homogeneous solution. The total solvent used in the chlorohydrin formation reaction can range generally from about 0 parts by weight to about 90 parts by weight, preferably from about 1 part by weight to about 60 parts by weight, and more preferably from about 5 parts by weight to about 40 parts by weight, per every 1 part by weight of divinylarene used.

The optional surfactant useful in the process of the present invention may include for example sodium dodecylbenzene sulfonate, C14-C16 alkyldimethylbenzyl-ammonium chloride, nonylphenol ethoxylate of 6 to 12 ethylene oxide units, and mixtures thereof.

The total surfactant used in the chlorohydrin formation reaction can range generally from about 0 part by weight to about 10 parts by weight, preferably from about 0.1 part by weight to about 5 parts by weight; and more preferably from about 0.5 part by weight to about 2 parts by weight; and most preferably from about 1 parts by weight to about 1.5 part by weight, per 100 parts by weight of divinylarene used.

In the second step of the process of the present invention, i.e., the dehydrohalogenation reaction step, a chlorohydrin from step (a) is converted to an epoxide by treating the chlorohydrin with at least one base compound, and optionally in the presence of a phase transfer agent and/or a solvent.

The chlorohydrin used in the second step of the process of the present invention is the chlorohydrin produced in step (b) above.

The concentration of the chlorohydrin used in the present invention may range generally from about 10 wt % to about 70 wt %, preferably from about 20 wt % to about 50 wt %, and more preferably from about 25 wt % to about 35 wt % based on the total weight of the dehydrohalogenation reaction composition.

The base compound useful in the process of the present invention may include for example any conventional basic material known in the art such as sodium hydroxide or potassium hydroxide and the like, for instance an aqueous solution with 20% sodium hydroxide. Generally, the molar ratio of base compound to chlorohydrin groups used in the present invention is preferably in the range of from about 0.9 to about 1.1.

The treatment step (b) may optionally include at least one phase transfer catalyst, and/or at least one dehydrohalogenation solvent. The optional phase transfer agent useful in the process of the present invention for the chlorohydrin conversion may include for example tetraalkyl, tetraphenyl, or mixed alkyl and aryl ammonium salts such as benzyltrimethylammonium chloride (BTMAC), and the like; and mixtures thereof. In another embodiment, an alcohol can be used as the phase transfer agent, such as for example isopropyl alcohol or 1-methoxy-2-propanol, such as Dowanol PM commercially available from The Dow Chemical Company; or mixtures thereof.

The concentration of the phase transfer agent used in the present invention may range generally from about 0.05 wt % to about 30 wt %, preferably from about 0.1 wt % to about 20 wt %, and more preferably from about 0.1 wt % to about 10 wt % based on the total weight of the composition. The concentration of ammonium salts when used may be more toward the lower end of the ranges, whereas when using alcohols the concentrations may be toward the upper end of the above ranges.

The optional dehydrohalogenation solvent useful in the second step of the process of the present invention may include for example any inert organic solvent that is inert to strong bases under the reaction conditions. For example, the solvent may include halogenated alkanes such as dichloromethane; aromatics such as toluene, xylene; hydrocarbon solvents such as hexane and pentene; ethers such as dimethoxyethane; ketones such as acetone, methylisobutyl ketone, or methylethyl ketone; and mixtures thereof. In another embodiment, a portion of the solvent may include any unreacted divinylarene present in the chlorohydrin starting material.

The concentration of the solvent used in the second step of the present invention may range generally from about 0 wt % to about 90 wt %, preferably from about 1 wt % to about 50 wt %, and more preferably from about 10 wt % to about 40 wt % based on the total weight of the composition.

The preparation of divinylarene dioxides with minimal co-production of undesirable by-products may be achieved by adding to a reactor the following reactants: (i) at least one divinylarene; (ii) hypochlorous acid; and (iii) water; and optionally (iv) solvent and/or optionally (v) surfactant; and allowing the reactant components to react under reaction conditions to form the chlorohydrins of the present invention in a first step.

The hypochlorination reaction conditions for the first step include carrying out the reaction of the reactants under a temperature, generally in the range of from about −10° C. to about 100° C., preferably from about 5° C. to about 80° C., and more preferably from about 20° C. to about 60° C.

In one preferred embodiment, the HOCl is not added all at once but instead is added slowly at a constant rate to the reaction mixture over a period of time sufficient to maintain the desired reaction temperature. In another embodiment, the HOCl is added slowly at a constant rate to the reaction mixture over a period of time of from 30 minutes to 2 hours.

The pressure of the hypochlorination reaction in the first step may be generally from about 0.1 atmosphere (atm) to about 10 atm.

The process of preparing a divinylarene dioxide of the present invention continues with a second step (i.e., the dehydrohalogenation step of the present invention) including adding to a reactor the following reactants: (vi) the chlorohydrins formed in the first step; and (vii) a base compound; (viii) optionally a phase transfer agent; and (ix) optionally a solvent; and allowing the reactant components to react under reaction conditions to produce a divinylarene dioxide.

The chlorohydrins formed in the first step including the hypochlorination reaction mixture effluent from the first step may be used as is directly in the dehydrohalogenation second step as the chlorohydrins are formed. In another embodiment, the chlorohydrins can be separated from the reaction mixture of the first step prior to the dehydrohalogenation second step. The separation of the chlorohydrins from the reaction mixture may be carried out by any well known means in the art such as by extraction using a solvent such as for example toluene, methylene chloride or mixtures thereof.

For example, in one embodiment, the chlorohydrins may be extracted into methylene chloride, then the extraction mixture can be separated into an organic phase and an aqueous phase, and then the organic phase may be stripped to remove the solvent. The crude chlorohydrins may then be dissolved in a solvent, for example, toluene-isopropyl alcohol, and the epoxidized, i.e., formed into the divinylarene dioxides. In another embodiment, the chlorohydrins may be formed into the divinylarene dioxides directly without a solvent.

The reaction conditions for the second step to manufacture the divinylarene dioxides, such as DVBDO, include carrying out the reaction of the reactants under a temperature, generally in the range of from about 0° C. to about 100° C., preferably from about 5° C. to about 80° C., and more preferably from about 20° C. to about 60° C.

The pressure of the dehydrohalogenation reaction in the second step may be generally from about 0.1 atmosphere (atm) to about 10 atm.

The overall process of the present invention, and/or any of the steps thereof, may be a batch or a continuous process. The reactor used in the process may be any reactor and ancillary equipment well known to those skilled in the art.

In addition to the reaction above, the process of the present invention may include further processing steps such as a method of separating any co-products formed during the reaction from product. The separation method may include for example any separation process and equipment well known to those skilled in the art.

For example, during the second step of the reaction for the preparation of divinylarene dioxides, equivalent amount of sodium chloride by-product which may be formed can be removed by separation of the organic and aqueous phases followed by the appropriate water washes of the organic phase.

After the two-step reactions of the present invention, the undesirable by-products; and any remaining additives and solvent, may be removed to recover a usable divinylarene dioxide product. Then the product may optionally be purified by well-known means in the art such as by distillation, crystallization, and the like.

One advantage of the present invention process is that high yields of divinylarene dioxides may be produced by the process of the present invention. With high yields of divinylarene dioxides produced, the process of the present invention advantageously requires less recycle and produces less waste.

The high yield of the divinylarene dioxides produced by the process of the present invention is generally greater than about 30% up to about 100%, based on divinylarene starting material. In one embodiment, the yield may range from about 40% to about 60%, based on divinylarene starting material. In another embodiment, the yield may range from about 40% to about 55%, based on divinylarene starting material.

The divinylarene dioxides prepared by the process of the present invention, particularly those derived from divinylbenzene such as for example divinylbenzene dioxide (DVBDO), are class of diepoxides which have a relatively low liquid viscosity but a higher rigidity than conventional epoxy resins.

The divinylarene dioxide prepared by the process of the present invention may comprise, for example, any substituted or unsubstituted arene nucleus bearing two vinyl groups in any ring position. The arene portion of the divinylarene dioxide may consist of benzene, substituted benzenes, or (substituted) ring-annulated benzenes or homologously bonded (substituted) benzenes, or mixtures thereof. The divinylbenzene portion of the divinylarene dioxide may be ortho, meta, or para isomers or any mixture thereof. Additional substituents may consist of oxidant-resistant groups including saturated alkyl, aryl, halogen, nitro, isocyanate, or RO— (where R may be a saturated alkyl or aryl). Ring-annulated benzenes may consist of naphthlalene, tetrahydronaphthalene, and the like. Homologously bonded (substituted) benzenes may consist of biphenyl, diphenylether, and the like.

The divinylarene oxide product prepared by the process of the present invention may be illustrated generally by general chemical Structures I-IV as follows:

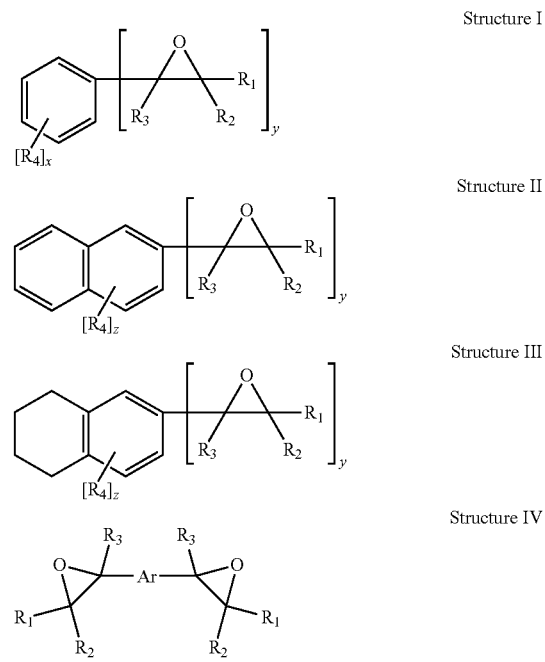

In the above Structures I, II, III and IV of the divinylarene dioxide product of the present invention, each $R_1$, $R_2$, $R_3$ and $R_4$ individually may be hydrogen, an alkyl, cycloalkyl, an aryl or an aralkyl group; or a oxidant-resistant group including for example a halogen, a nitro, an isocyanate, or an RO group, wherein R may be an alkyl, aryl or aralkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, 1,3-phenylene group.

The divinylarene dioxide product produced by the process of the present invention may include for example alkyl-vinylarene monoxides depending on the presence of alkylvinylarene in the starting material.

In one embodiment of the present invention, the divinylarene dioxide produced by the process of the present invention may include for example divinylbenzene dioxide, divinylnaphthalene dioxide, divinylbiphenyl dioxide, divinyldiphenylether dioxide, and mixtures thereof.

In a preferred embodiment of the present invention, the divinylarene dioxide used in the epoxy resin formulation may be for example DVBDO. Most preferably, the divinylarene dioxide component that is useful in the present invention includes, for example, a divinylbenzene dioxide as illustrated by the following chemical formula of Structure V:

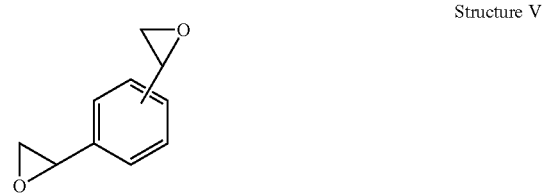

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which have a relatively low liquid viscosity but a higher rigidity and crosslink density than conventional epoxy resins.

Structure VI below illustrates an embodiment of a preferred chemical structure of a DVBDO useful in the present invention:

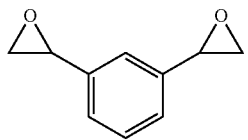

Structure VI

Structure VII below illustrates another embodiment of a preferred chemical structure of the DVBDO useful in the present invention:

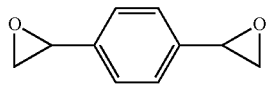

Structure VII

When DVBDO is prepared by the processes of the present invention, it is possible to obtain one of three possible isomers: ortho, meta, and para. Accordingly, the present invention includes a DVBDO illustrated by any one of the above Structures individually or as a mixture thereof. Structures VI and VII above show the meta (1,3-DVBDO) isomer and the para (1,4-DVBDO) isomer of DVBDO, respectively. The ortho isomer is rare; and usually DVBDO is mostly produced generally in a range of from about 9:1 to about 1:9 ratio of meta isomer (Structure VI) to para isomer (Structure VII). The present invention preferably includes as one embodiment a range of from about 6:1 to about 1:6 ratio of Structure VI to Structure VII, and in other embodiments the ratio of Structure VI to Structure VII may be from about 4:1 to about 1:4 or from about 2:1 to about 1:2.

In one embodiment, the process of the present invention is particularly suited for the preparation of divinylbenzene dioxide, a low viscosity liquid epoxy resin. The viscosity of the divinylarene dioxides produced by the process of the present invention ranges generally from about 10 mP-s to about 100 mP-s; preferably, from about 10 mP-s to about 50 mP-s; and more preferably, from about 10 mP-s to about 25 mP-s at 25° C.

The utility of the divinylarene dioxides of the present invention requires their thermal stability to allow their formulation or processing at moderate temperatures (for example, at from about 100° C. to about 200° C.) for up to several hours (for example, for at least 2 hours) without oligomerization or homopolymerization. Oligomerization or homopolymerization during formulation or processing is evident by a substantial increase in viscosity or gelling (crosslinking). The divinylarene dioxides of the present invention have sufficient thermal stability such that they do not experience a substantial increase in viscosity or gelling during formulation or processing at moderate temperatures.

The divinylarene dioxide products of the present invention are useful for the preparation of epoxy resin compositions or formulations which, in turn, are useful for preparing thermosets or cured products in the form of coatings, films, adhesives, laminates, composites, electronics, and the like.

As an illustration of the present invention, in general, resin compositions based on the divinylarene dioxide products of the present invention may be useful for casting, potting, encapsulation, molding, and tooling. The present invention is particularly suitable for all types of electrical casting, potting, and encapsulation applications; for molding and plastic tooling; and for the fabrication of vinyl ester resin based composites parts, particularly for producing large vinyl ester resin-based parts produced by casting, potting and encapsulation. The resulting composite material may be useful in some applications, such as electrical casting applications or electronic encapsulations, castings, moldings, potting, encapsulations, injection, resin transfer moldings, composites, coatings and the like.

EXAMPLES

The following examples and comparative examples further illustrate the present invention in detail but are not to be construed to limit the scope thereof.

The various terms and designations used in the following Examples include for example the following: DVB stands for divinylbenzene and DVB, 80% technical, is commercially available from Aldrich; NaOCl is sodium hypochlorite and NaOCl, 12.5 wt % solution in water, is commercially available from Aldrich; HOCl stands for hypochlorous acid and a HOCl acid solution (4.2 wt %) is used in the Examples; carbon dioxide ($CO_2$) is commercially available from BOC gases; DVBDCH stands for divinylbenzene dichlorohydrin; EVBMCH stands for ethylvinylbenzene monochlorohydrin; DDBSNa stands for dodecylbenzene sulfonic acid, sodium salt and DDBSNa is commercially available from Aldrich; and toluene, isopropyl alcohol, methylene chloride ($MeCl_2$) and 50% sodium hydroxide (NaOH) solution are commercially available from Fisher Scientific.

Gas Chromatography (GC) Analysis

The product mixtures prepared in the Examples which follow were analyzed by standard gas chromatography (GC) analytical equipment and methods. Identification of peaks in GC was determined by GC mass spectrometry analysis. GC area percent and weight percent methods were used to monitor reaction progress and for analysis of crude products after workup. GC weight percent analysis was done using diglyme as the internal standard. Hypochlorination reaction samples were extracted with dichloroethane prior to GC analysis. A known weight of the organic layer from the extraction (~2.0 g) was mixed with a known weight of diglyme (~0.02 g) and analyzed by GC. A pure sample of DVBDCH was not available for GC weight percent method development, so GC area percent was used for DVBDCH. GC weight percent was used in addition to area percent for DVB and DVBDO.

The yields set forth in the Examples were calculated as follows:

Percent Yield of DVBDCH Based on DVB Charged

The yield of DVBDCH in grams was calculated from the mass of crude product after solvent removal and the approximate weight ratio of DVBDCH in the crude DVBDCH as measured by GC. The formulas used to calculate percent yield of DVBDCH based on divinylbenzene charged may be written as follows:

DVBDCH yield (gram)=(weight of crude DVBDCH after solvent removal)×(GC area ratio of DVB-DCH in crude product).

Theoretical DVBDCH yield based on DVB charged, gram=[(weight of DVB reagent charged)× (weight ratio of DVB in reagent)/(130.2 g DVB/ mol)]×235.1 g DVBDCH/mol.

DVBDCH yield (%)=(DVBDCH yield, gram/theoretical DVBDCH yield, gram)×100%.

Percent Yield of DVBDO Based on DVB Charged in Hypochlorination Reaction

The yield of DVBDO in grams was calculated from the mass of crude product after epoxidation and the weight ratio of DVBDO in the crude as measured by an internal standard GC analysis method. The DVBDO yield was calculated by the following equations:

DVBDO yield (gram)=(weight of crude product)× (weight ratio DVBDO in crude product).

Theoretical DVBDO yield based on DVB charged, gram=[(weight of DVB reagent charged)× (weight ratio of DVB in reagent)/(130.2 g DVB/ mol)]×162.2 g DVBDO/mol.

DVBDO yield (%)=(DVBDO yield, gram/theoretical DVBDO yield, gram)×100%.

Example 1

Step (a)—Hypochlorination Reaction

Divinylbenzene (18.87 g, 0.1449 mol), DBBSNa (0.1887 g) and deionized water (445.1 g) were charged to a 1-Liter 5-neck flask, jacketed, with baffles, equipped with a mechanical stirrer, a NaOCl solution feed inlet, a $CO_2$ gas inlet (a fritted glass tube positioned below the liquid level in reactor) and a glycol cooled condenser. While vigorously stirring the resulting mixture at 20° C., injection of $CO_2$ gas was begun at 300 cc/min and shortly thereafter addition of 12.5% NaOCl solution was begun at a rate of a 0.52 g/min. A total of 155.2 g (0.2605 mol) of NaOCl solution was added over a period of five hours. The temperature was maintained at 20° C. by control of the jacket temperature using a glycol circulator bath. $CO_2$ injection was maintained throughout the entire experiment. The reaction progress was monitored by GC analysis. The final reaction mixture was diluted with deionized water (64 g) then extracted with methylene chloride (415 g). After mixing and allowing the phases to separate, the organic layer was drained and filtered through a Whatman No. 1 paper giving 355 g of clear liquid. Not counting the methylene chloride in the percentage calculation, the liquid had 43% DVBDCH (sum of meta and para isomers) based on GC area percent analysis.

Step (b)—Epoxidation Reaction

The methylene chloride was removed from the hypochorination reaction extract by evaporation, then the crude DVB-DCH (24.13 g, ~0.18 eq. of chlorohydrin, a solid at room temperature) was taken up in toluene (45.6 g) and transferred to a 250-mL 3-neck flask, jacketed, with baffles, equipped with mechanical stirrer and NaOH feed inlet. Isopropyl alcohol was added (11.4 g). The mixture was stirred vigorously at 55° C. whereupon 20% NaOH solution (36 g, 0.18 mol) was added over a period of 30 minutes. The mixture was digested one hour at 60° C., and then cooled to 10° C. Stirring was stopped and the layers were allowed to separate. The brine layer (39 g) was removed. The remaining organic layer was washed with 40 g of 2% sodium bicarbonate in water followed by two water washes with 40 g deionized water each time. The aqueous had pH 6-7 after the second water wash. The organic layer after the second water wash was 75.2 g. The organic layer contained no remaining DVBDCH and contained 7.2 wt % DVBDO by GC weight percent analysis. The DVBDCH yield for the hypochlorination reaction was calculated to be 38% based on DVB. The DVBDO yield after the epoxidation reaction was calculated to be 34% based on DVB charged.

Example 2

Hypochlorination Reaction

Divinylbenzene (19.0 g, 0.1459 mol), deionized water (253 g), and DDBSNa (0.197 g) were charged to a 1-Liter 5-neck flask, jacketed, with baffles, equipped with a mechanical stirrer, a hypochlorous acid (HOCl) feed inlet, and a glycol cooled condenser. The mixture was cooled to 6° C. with vigorous stirring whereupon a addition of a solution containing 4.16% HOCl in water (330.7 g, 0.2622 mol HOCl, pH 3.3) was begun at a rate of 2.75 g/min The HOCl solution was added over a period of 125 minutes with the temperature maintained at 9° C. then the reaction was digested an additional 45 minutes at 14° C. During the digest period, a solid was observed sticking to the top of reactor. The reaction mixture, containing some solids, was extracted twice with methylene chloride (total 307 g). After settling in separatory funnel the organic layer was drained and filtered through a Whatman No. 1 filter paper. The combined weight of organic extracts was 268 grams. The organic extracts were devolatilized in vacuo at 70° C. and 20 mmHg pressure yielding 24.4 g of crude DVBDCH containing 38.5% DVB-DCH by GC area percent analysis (sum of meta and para isomers) with the balance being EVBMCH along with undesired byproducts formed during the hypochlorination reaction. The percent yield of DVBDCH was 34%. The DVBDCH was not epoxidized.

Example 3

Hypochlorination Reaction

A solution with ~4.14% HOCl in water with pH 5.9 was prepared by dropwise addition of 50% NaOH (1.47 g) to a stirred solution of 4.16% HOCl (217.6 g, 0.1725 mol, pH 3.1). Divinylbenzene (10.0 g, 0.077 mol), acetone (300 g), and deionized water (41.5 g) were charged to 1-Liter 5-neck flask, jacketed, with baffles, equipped with a mechanical stirrer, a hypochlorous acid (HOCl) feed inlet, and a glycol cooled condenser. With vigorous stirring of the mixture, the pre-formed HOCl solution was added at a rate of 3.6 g/minute over a period of 60 minutes while allowing the reaction temperature to increase from ambient temperature (about 23° C.) to 30° C. The reaction was digested for one hour at 29° C. and then cooled to 20° C. The resulting clear homogeneous solution was extracted with methylene chloride (300 g) to give 545 g of organic layer. The remaining aqueous was extracted a second time with 150 g of methylene chloride giving 189 g of organic layer which GC showed had no DVBDCH. The first methylene chloride extract was devolatilized in vacuo at 70° C. and 20 mmHg pressure yielding 17.0 g of crude DVB-DCH which contained 40.2% DVBDCH (sum of meta and para isomers) by GC area percent analysis with the balance being EVBMCH along with undesired byproducts formed in the reaction. The percent yield of DVBDCH based on starting DVB was 47%. The DVBDCH was not epoxidized.

Example 4

Step (a)—Hypochlorination Reaction

Divinylbenzene (9.95 g, 0.077 mol), acetone (290 g), and deionized water (73.2 g) were charged to 1-Liter 5-neck flask, jacketed, with baffles, equipped with a mechanical stirrer, a hypochlorous acid (HOCl) feed inlet, and a glycol cooled condenser.

While vigorously stirring the resulting mixture, a 4.16% HOCl solution in water (174.06 g, 0.138 mol HOCl, pH 3.7) was added to the mixture at a feed rate of 2.9 g/minute. The HOCl solution was added over a period of 60 minutes while allowing the temperature to increase to 30° C. The mixture was cooled to 22° C., and then the resulting clear homogeneous solution was extracted with methylene chloride (290 g) followed by settling then separation of the resulting phases. Solvent was removed in vacuo at 70° C. and 20 mmHg pressure yielding 15.0 g of crude product which contained 51.9% DVBDCH (sum of meta and para isomers). The percent yield of DVBDCH was 55% based on DVB.

Step (b)—Epoxidation Reaction

The crude DVBDCH was dissolved in toluene-isopropanol solution (28.8 g toluene, 7.2 g IPA) and transferred to a jacketed reactor. The mixture was warmed to 55° C. with vigorous stirring whereupon a 20% NaOH solution (20.5 g) was added to the mixture over 30 minutes. The mixture was stirred an additional 60 minutes at 60° C., and then cooled to 20° C. The resulting layers formed in the reactor were allowed to settle, and then the resulting lower brine layer was removed. The remaining organic layer was washed once with 2% NaHCO3 solution (25 g), and then two times with deionized water (25 g per wash). The organic layer following the washes (32.5 g) was analyzed by GC and found to contain 14.5 wt % of DVBDO. After adjusting the yield for samples taken in both the hypochlorination and epoxidation reactions, the DVBDO yield was determined to be 56%.

The conditions and the results for the hypochlorination of divinylbenzene to divinylbenzenedichlorohydrin are summarized below in Table I.

TABLE I

| Example | HOCl source | NaOCl or HOCl/C=C equiv | C=C conc (mmol/mL) | (NaOCl or HOCl) feed time (hours) | H₂O/DVB (wt ratio) | Solvent | Surfactant | Solvent or Surfactant/DVB (wt ratio) | Temp. (° C.) | DVB conv (%) | DVBDCH % Yield[a] | Phase(s) |
|---|---|---|---|---|---|---|---|---|---|---|---|---|
| 1 | 12.5% NaOCl/CO₂ | 1 | 0.4783 | 5 | 30 | None | DDBSN a | 0.01 | 20 | 97.7 | 38 | 2 phase |
| 2 | 4.2% HOCl pH 3.3 | 1 | 0.4826 | 2 | 30 | None | DDBSN a | 0.01 | 9 | 98.5 | 34 | 2 phase |
| 3 | 4.2% HOCl pH adj to 6 | 1.25 | 0.2367 | 1 | 25 | Acetone | None | 30.00 | 22[b] | 98 | 47 | 1 phase |
| 4 | 4.2% HOCl pH 3.66 | 1 | 0.2208 | 1 | 24 | Acetone | None | 29.00 | 22[b] | 100 | 55 | 1 phase |

Footnotes for Table I:
[a] DVBDCH Yield calculated from weight of stripped chlorohydrin and GC area % of DVB-DCH
[b] Started at ambient and did not provide temperature control. Temperature reached maximum of 29 C.-30 C.

What is claimed is:

1. A process for preparing a divinylarene dioxide comprising
   (a) reacting, at a temperature of from −10° C. to about 100° C. and at a pressure, of from about 0.1 atmosphere to about 10 atmospheres, at least one divinylarene with hypochlorous acid to form a chlorohydrin, in the presence of a water; and
   (b) treating, at a temperature of from 0° C. to about 100° C. and at a pressure of from about 0.1 atmosphere to about 10 atmospheres, the chlorohydrin formed in step (a) with at least one base to form a divinylarene dioxide product.

2. The process of claim 1, wherein the divinylarene in step (a) is divinylbenzene; and wherein the divinylarene dioxide formed is divinylbenzene dioxide.

3. The process of claim 1, wherein the hypochlorous acid is pre-formed in a separate step prior to adding the hypochlorous acid to the reaction in step (a).

4. The process of claim 1, wherein the hypochlorous acid is formed in situ by the reaction of (i) chlorine and water; or (ii) an alkali metal hypochlorite and an acid.

5. The process of claim 1, wherein the reaction of step (a) includes a hypochlorination solvent.

6. The process of claim 1, wherein the divinylarene is divinylbenzene; wherein the hypochlorous acid is a pre-formed hypochlorousacid; and wherein the hypochlorination solvent is acetone.

7. The process of claim 1, wherein the reaction of step (a) includes at least one surfactant and wherein the base in step (b) is an alkali metal hydroxide.

8. The process of claim 1, wherein the treatment of step (b) includes at least one phase transfer agent; or wherein the treatment of step (b) includes at least one dehydrohalogenation solvent.

9. The process of claim 1, wherein the reaction of step (a) is carried out at a temperature within the range of from about 0° C. to about 100° C.; wherein the pH of the pre-formed hypochlorous acid comprises from about 3 to about 7.

10. The process of claim 1, wherein the concentration of the divinylarene in step (a) ranges from about 0.5 weight percent to about 100 weight percent; wherein the mole ratio of the hypochlorous acid to the olefinic C=C, groups of the divinylarene ranges from about 0.5 to about 1.5; and wherein the total water used in the chlorohydrin formation reaction of step (a) ranges from about 5 parts by weight to about 50 parts by weight.

11. The process of claim 1, wherein the concentration of the chlorohydrin in step (b) ranges from about 10 weight percent to about 70 weight percent; and wherein the molar ratio of the base compound to the chlorohydrin groups of the chlorohydrin in step (h) ranges from about 0.9 to about 1.1.

12. The process of claim 1, including step (c) purifying the divinylarene dioxide reaction product.

13. The process of claim 1, wherein the hypochlorous acid consists of a solution of hypochlorous acid dissolved in an organic solvent; wherein said hypochlorous acid solution is free of chloride ions; and wherein said hypochlorous acid solution is obtained by extracting hypochlorous acid from a hypochlorous acid reaction mixture with the organic solvent.

14. The process of claim 13, wherein the solution of hypochlorous acid in organic solvent contains from about 0.1 to about 50 percent by weight of hypochlorous acid.

* * * * *